United States Patent
Wu et al.

(10) Patent No.: US 11,257,251 B2
(45) Date of Patent: Feb. 22, 2022

(54) METHODS AND DEVICES FOR GUIDING A PATIENT

(71) Applicant: SHANGHAI UNITED IMAGING INTELLIGENCE CO., LTD., Shanghai (CN)

(72) Inventors: Ziyan Wu, Lexington, MA (US); Shanhui Sun, Lexington, MA (US); Arun Innanje, Lexington, MA (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 294 days.

(21) Appl. No.: 16/657,125

(22) Filed: Oct. 18, 2019

(65) Prior Publication Data
US 2021/0118174 A1  Apr. 22, 2021

(51) Int. Cl.
| | |
|---|---|
| G06K 9/00 | (2006.01) |
| A61B 5/05 | (2021.01) |
| G06T 7/73 | (2017.01) |
| G06T 7/136 | (2017.01) |
| G16H 40/67 | (2018.01) |
| G16H 70/00 | (2018.01) |
| G06T 7/00 | (2017.01) |

(52) U.S. Cl.
CPC ............. *G06T 7/75* (2017.01); *G06T 7/0012* (2013.01); *G06T 7/136* (2017.01); *G16H 40/67* (2018.01); *G16H 70/00* (2018.01); *G06T 2207/10028* (2013.01)

(58) Field of Classification Search
USPC ................ 382/100, 103, 106, 128–132, 155, 382/172–173, 181, 199, 219, 224, 254, 382/286–291, 305; 378/4, 21, 37; 600/411, 415
See application file for complete search history.

(56) References Cited

U.S. PATENT DOCUMENTS

| | | | | |
|---|---|---|---|---|
| 8,571,174 | B2 * | 10/2013 | Smith | A61B 6/025 378/37 |
| 2008/0249396 | A1 * | 10/2008 | Biglieri | G06T 7/0012 600/411 |
| 2017/0337732 | A1 * | 11/2017 | Tamersoy | G06K 9/6256 |
| 2019/0126068 | A1 * | 5/2019 | Vilsmeier | G16H 10/60 |
| 2019/0366030 | A1 * | 12/2019 | Giap | G16H 40/63 |
| 2020/0368555 | A1 * | 11/2020 | Gou | A61N 5/1067 |
| 2021/0169367 | A1 * | 6/2021 | Mahfouz | G16H 50/20 |

* cited by examiner

*Primary Examiner* — Seyed H Azarian
(74) *Attorney, Agent, or Firm* — Faegre Drinker Biddle & Reath LLP

(57) ABSTRACT

Methods and systems for guiding a patient for a medical examination using a medical apparatus. For example, a computer-implemented method for guiding a patient for a medical examination using a medical apparatus includes: receiving an examination protocol for the medical apparatus; determining a reference position based at least in part on the examination protocol; acquiring a patient position; determining a deviation metric based at least in part on comparing the patient position and the reference position; determining whether the deviation metric is greater than a pre-determined deviation threshold; and if the deviation metric is greater than a pre-determined deviation threshold: generating a positioning guidance based at least in part on the determined deviation metric, the positioning guidance including guidance for positioning the patient relative to the medical apparatus.

19 Claims, 4 Drawing Sheets

METHODS AND DEVICES FOR GUIDING A PATIENT

1. BACKGROUND OF THE INVENTION

Certain embodiments of the present invention are directed to image processing. More particularly, some embodiments of the invention provide methods and devices for medical image processing. Merely by way of example, some embodiments of the invention have been applied to guiding a patient for a medical examination using a medical apparatus. But it would be recognized that the invention has a much broader range of applicability.

Patient positioning during a medical imaging scan is a complex problem. Conventionally, there are hundreds of combinations of standard poses corresponding to various types of scans (e.g., CT, MR, X-ray, PET, etc.) as well as various scanning protocols. It is often difficult for a patient to perform or pose the standard pose during a scan, especially for an injured or elderly patient. Additionally, it is challenging for a medical staff (e.g., a scan technician), who in conventional clinical practice often help positions the patient, to visually judge the positioning correctness of the patient's pose in respect to the standard pose. In particularly, it is especially difficult for scans involving a trauma patient or patient with additional medical equipment or accessories coupled to the patient's body. At least owing to the challenges described, medical imaging scans often produce images with unsatisfactory image quality insufficient for diagnosis. As a result, rescans are often performed, leading to reduction in efficiency. It is therefore desirable to have a method or system for patient positioning for reducing patient positioning errors, improving scanning efficiency, reducing technician workload, and improving scanned image quality for better diagnosis.

2. BRIEF SUMMARY OF THE INVENTION

Certain embodiments of the present invention are directed to image processing. More particularly, some embodiments of the invention provide methods and devices for medical image processing. Merely by way of example, some embodiments of the invention have been applied to guiding a patient for a medical examination using a medical apparatus. But it would be recognized that the invention has a much broader range of applicability.

In various embodiments, a computer-implemented method for guiding a patient for a medical examination using a medical apparatus includes: receiving an examination protocol for the medical apparatus; determining a reference position based at least in part on the examination protocol; acquiring a patient position; determining a deviation metric based at least in part on comparing the patient position and the reference position; determining whether the deviation metric is greater than a pre-determined deviation threshold; and if the deviation metric is greater than a pre-determined deviation threshold: generating a positioning guidance based at least in part on the determined deviation metric, the positioning guidance including guidance for positioning the patient relative to the medical apparatus.

In various embodiments, a system for guiding a patient for a medical examination using a medical apparatus includes: a protocol receiving module configured to receive an examination protocol for the medical apparatus; a reference position determining module configured to determine a reference position based at least in part on the examination protocol; a patient position acquiring module configured to acquire a patient position; a deviation metric determining module configured to determine a deviation metric based at least in part on comparing the patient position and the reference position; a positioning guidance module configured to: determine whether the deviation metric is greater than a pre-determined deviation threshold; and if the deviation metric is greater than a pre-determined deviation threshold: generate a positioning guidance based at least in part on the determined deviation metric. In certain examples, the positioning guidance including guidance for positioning the patient relative to the medical apparatus. In certain examples, the patient position acquiring module is further configured to acquire a second patient position.

In various embodiments, a non-transitory computer-readable medium with instructions stored thereon, that when executed by a processor, perform the processes including: receiving an examination protocol for the medical apparatus; determining a reference position based at least in part on the examination protocol; acquiring a patient position; determining a deviation metric based at least in part on comparing the patient position and the reference position; determining whether the deviation metric is greater than a pre-determined deviation threshold; and if the deviation metric is greater than a pre-determined deviation threshold: generating a positioning guidance based at least in part on the determined deviation metric, the positioning guidance including guidance for positioning the patient relative to the medical apparatus.

Depending upon embodiment, one or more benefits may be achieved. These benefits and various additional objects, features and advantages of the present invention can be fully appreciated with reference to the detailed description and accompanying drawings that follow.

3. BRIEF DESCRIPTION OF THE DRAWINGS

4. DETAILED DESCRIPTION OF THE INVENTION

Certain embodiments of the present invention are directed to image processing. More particularly, some embodiments of the invention provide methods and devices for medical image processing. Merely by way of example, some embodiments of the invention have been applied to guiding a patient for a medical examination using a medical apparatus. But it would be recognized that the invention has a much broader range of applicability.

Figure 1:
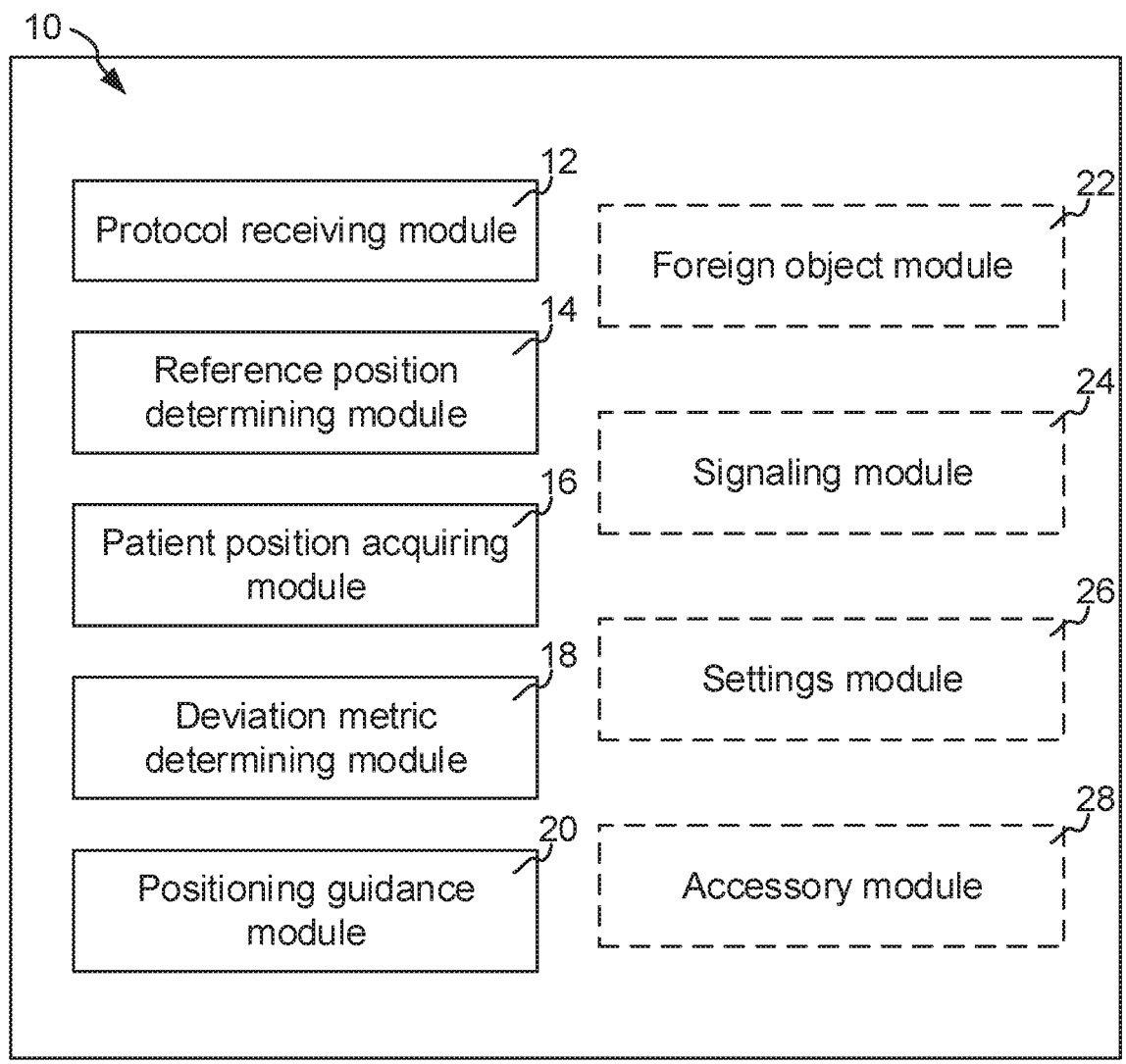
FIG. 1 is a simplified diagram showing a system for guiding a patient for a medical examination using a medical apparatus, according to some embodiments of the present invention.

FIG. 1 is a simplified diagram showing a system for guiding a patient for a medical examination using a medical apparatus, according to some embodiments of the present invention. This diagram is merely an example, which should not unduly limit the scope of the claims. One of ordinary skill in the art would recognize many variations, alternatives, and modifications. In some examples, the system 10 includes a protocol receiving module 12, a reference position determining module 14, a patient position acquiring module 16, a deviation metric determining module 18, and/or a positioning guidance module 20. In certain examples, the system 10 further includes a foreign object module 22, a signaling module 24, a settings module 26, and/or an accessory module 28. In some examples, the system 10 is a patient position guidance system configured to guide a patient towards a target position (e.g., a reference position such as a standardized position), such as for medical image acquisition (e.g., an X-ray scan), surgical procedures, patient care, and/or physical therapy. Although the above has been shown using a selected group of components, there can be many alternatives, modifications, and variations. For example, some of the components may be expanded and/or combined. Other components may be inserted to those noted above. Depending upon the embodiment, the arrangement of components may be interchanged with others replaced.

In various embodiments, the protocol receiving module 12 is configured to receive an examination protocol, such as an examination protocol for the medical apparatus. In some examples, the examination protocol is selected by a user. For example, the examination protocol can be selected by a use from a menu, such as a drop-down menu. In certain examples, the examination protocol corresponds to one or more parameters of the medical apparatus. In various examples, the examination protocol is a scanning protocol.

In various embodiments, the reference position determining module 14 is configured to determine a reference position based at least in part on the examination protocol. In some examples, the reference position is a standard position corresponding to the examination protocol. In certain examples, the reference position determining module 14 is configured to automatically determine the reference position. In various examples, the reference position determining module 14 is configured to determine the reference position based at least in part on patient information such as patient gender, age, and/or measurements. In some examples, the reference position is a template position corresponding to a standard pose, which may correspond to an examination protocol.

In various embodiments, the patient position acquiring module 16 is configured to acquire a first patient position. In some examples, the first patient position corresponds to a patient position of a patient before the patient is adjusted according to a positioning guidance. In certain examples, the patient position acquiring module 16 is further configured to acquire a second patient position. In some examples, the second patient position corresponds to a patient position of the patient after the patient is adjusted according to the positioning guidance. In various examples, the patient position acquiring module 16 is configured to acquire a first patient image and generate the first patient position based at least in part on the first patient image. In some examples, the patient position acquiring module 16 is configured to acquire the first patient image using a sensor. In certain examples, the sensor includes a RGB sensor, a RGBD sensor, a laser sensor, a FIR sensor, a NIR sensor, and/or a lidar sensor. In some examples, the sensor includes a plurality of sensors, such as arranged as a sensor array.

In various embodiments, the patient position acquiring module 16 is configured to generate the first patient position based at least in part on the first patient image using a feature extraction model (e.g., a neural network trained for extracting one or more features). In certain embodiments, the patient position acquiring module 16 is configured to determine one or more internal landmarks associated with the acquired first patient image. In some examples, the one or more internal landmarks includes an anatomical feature (e.g., a rib or a joint). In some embodiments, the patient position acquiring module 16 is further configured to determine one or more external landmarks associated with the acquired first patient image. In certain examples, the one or more external landmarks includes a non-anatomical object (e.g., a medical reference accessory). In various embodiments, the patient position acquiring module 16 is configured to generate a first patient representation. In certain examples, the first patient representation is two-dimensional or three-dimensional. In some examples, the patient representation includes an image, a kinematic model, a skeleton model, a surface model, a mesh model, a point cloud, and/or a feature list including one or more features each having a corresponding coordinate (e.g., within a scan volume of the scanning apparatus). In some examples, the patient acquiring module 16 is configured to generate patient representation using a neural network (e.g., a convolutional neural network), such as a neural network trained for generating patient representation. In certain examples, the neural network trained for generating patient representation is the same neural network trained for extracting one or more features.

In various embodiments, the deviation metric determining module 18 is configured to determine a first deviation metric. For example, the deviation metric determining module 18 is configured to determine the first deviation metric based at least in part on the first patient position (e.g., position before adjustment according to a positioning guidance) and the reference position (e.g., standard position according to an examination protocol). For example, the deviation metric determining module 18 is configured to determine the first deviation metric based at least in part on comparing (e.g., determining a difference between) the first patient position and the reference position. In various examples, the first deviation metric is a score, a matrix, or a vector. In some embodiments, the deviation metric determining module 18 is configured to determine a second deviation metric. For example, the deviation metric determining module 18 is configured to determine the second deviation metric based at least in part on the second patient position (e.g., position after adjustment according to a positioning guidance) and the reference position (e.g., standard position according to an examination protocol). For example, the deviation metric determining module 18 is configured to determine the second deviation metric based at least in part on comparing (e.g., determining a difference between) the second patient position and the reference position. In various examples, the second deviation metric is a score, a matrix, or a vector.

In certain embodiments, the deviation metric determining module 18 is configured to determine a reference vector based at least in part on the reference position, determine a first patient vector based at least in part on the first patient position, determine a first deviation vector based at least in part on the reference vector and the first patient vector, and determine the first deviation metric based at least in part on the first deviation vector. As an example, the deviation metric determining module 18 is configured to determine a distance (e.g., Euclidean distance) between the first patient vector and the reference vector and determine the deviation metric and/or a similarity metric based at least in part on the determined distance (e.g., Euclidean distance). In various embodiments, the deviation metric determining module 18 is configured to determine one or more anatomical features.

For example, the determined one or more anatomical features is associated with (e.g., pertinent to) the medical examination.

In various examples, the deviation metric determining module 18 is configured to classify the first deviation vector as irrelevant if the first deviation vector is determined based on an anatomical feature that is not included in the one or more anatomical features, and classify the first deviation vector as relevant if the first deviation vector is determined based on an anatomical feature that is included in the one or more anatomical features. For example, for a fractured rib examination, the deviation metric determining module 18 is configured to classify an arm deviation vector determined based on the arm (e.g., an arm vector and a reference arm vector) to be irrelevant, whereas the deviation metric determining module 18 is configured to classify a rib-deviation vector determined based on the rib (e.g., a rib vector and a reference rib vector) to be relevant. In some examples, a deviation metric corresponds to a similarity metric (e.g., a similarity score). In certain examples, the deviation metric determining module 18 is configured to determine a deviation metric based on part of a patient body.

In various embodiments, the positioning guidance module 20 is configured to determine whether the first deviation metric is greater than a pre-determined deviation threshold. For example, the pre-determined deviation threshold is selected by a user, such as via a menu. In some examples, the positioning guidance module 20 is further configured to, if the first deviation metric is determined to be greater than (e.g., corresponding to a dissatisfactory patient position) a pre-determined deviation threshold, generate a first positioning guidance based at least in part on the determined first deviation metric. In certain examples, the first positioning guidance includes guidance for positioning the patient relative to the medical apparatus. In some examples, the first positioning guidance includes guidance for the patient or a medical staff to adjust the patient or the medical apparatus (e.g., an X-ray tube). In certain examples, the positioning guidance module 20 is configured to determine whether the second deviation metric is greater than (e.g., corresponding to a dissatisfactory patient position) the pre-determined deviation threshold. In some examples, a positioning guidance includes guidance for adjusting the patient from the patient position towards (e.g., to fit) the reference position, such as until the deviation between an adjusted position of the adjusted patient and the reference position is lesser than a predetermined acceptable deviation level.

In some embodiments, the positioning guidance module 20 is configured to present the first positioning guidance continuously, such as to present the first positioning guidance live with real-time or near real-time update. In certain examples, the positioning guidance module 20 is configured to present the first positioning guidance statically, such as to present the first positioning guidance as fixed. In various examples, the positioning guidance module 20 is configured to generate a visual guidance and/or an audio guidance. In some embodiments, the positioning guidance module 20 is configured to generate, as the visual guidance, a visual representation on a display screen, a hologram in the three-dimensional space, a two-dimensional projection from a projector, an augmented reality representation in an augmented reality eyewear, a virtual reality representation in a virtual reality eyewear, and/or a lighting cue indicated by a light-emitting device. In certain examples, the positioning guidance module 20 is configured to generate the audio guidance (e.g., via a speaker) having an audio volume corresponding to a magnitude of the deviation metric. In some examples, the positioning guidance module 20 is configured to generate an overlay highlighting the first deviation metric associated with the first patient position and the reference position. In various examples, the positioning guidance module 20 is configured to present the overlay overlaid onto the first patient position or the first patient image. In certain examples, the positioning guidance module 20 is configured to present the reference position for guiding the positioning of the patient.

In some embodiments, the foreign object module 22 is configured to detect a foreign object based at least in part on the acquired first patient image. For example, the foreign object includes a blocking object that can block the medical apparatus from following a path according to a protocol, an opaque (e.g., radiation-opaque) object to the medical apparatus (e.g., an X-ray scanner) that can block pertinent anatomical features, and/or an interfering (e.g., radiation-interfering) object which can lead to poor image quality. In various examples, the foreign object module 22 is configured to generate a collision avoidance based at least in part on the foreign object, such as to generate a collision avoidance based at least in part on the location and/or the dimensions of the foreign object (e.g., a device, a part of the patient, a part of a medical staff). In certain examples, the collision avoidance includes a pause scan instruction, a stop scan instruction, an audio alert, a visual alert, and an/or overriding re-routing scan path (e.g., a path avoiding collision with the foreign object).

In some embodiments, the signaling module 24 is configured to generate a signal for indicating that the patient is ready for examination (e.g., medical examination), such as if the first deviation metric is smaller than or equal to (e.g., corresponding to a satisfactory patient position) the pre-determined deviation threshold. In various examples, the signaling module 24 is configured to generate a signal for indicating that the patient is ready for examination using an examination setting. In certain examples, the signal for indicating that the patient is ready for examination includes a visual signal and/or an audio signal. In some examples, the signaling module 24 is further configured to present the signal for indicating that the patient is ready, such as via a display, such as via a user interface.

In some embodiments, the settings module 26 is configured to determine the examination setting. In certain examples, the examination setting includes a scanning path, a scanning angulation, a scanning parameter, a scanning speed, a scanning dose, and/or patient information. In certain examples, the settings module 26 is further configured to determine the examination setting in real-time based at least in part on the reference position and/or the first patient position. In some examples, the settings module 26 is configured to select the examination setting from a plurality of pre-determined examination settings.

In some embodiments, the accessory module 28 is configured to determine a reference accessory position, acquire a first accessory position, and determine a first accessory deviation metric based at least in part on the first accessory position and the reference accessory position. In certain examples, the accessory module 28 includes and/or controls a protocol receiving module (e.g., protocol receiving module 12), a reference position determining module (e.g., reference position determining module 14), a patient position acquiring module (e.g., patient position acquiring module 16), a deviation metric determining module (e.g., deviation metric determining module 18), and/or a positioning guidance module (e.g., positioning guidance module 20). In various examples, the accessory module 28 is configured to determine the first accessory deviation metric based at least in part on comparing (e.g., determining a difference between) the first accessory position and the reference accessory position. In various examples, the accessory module 28 is configured to determine whether the first accessory deviation metric is greater than a pre-determined accessory deviation threshold. The pre-determined accessory deviation threshold may be selected by a user, such as via a menu.

In some examples, the accessory module 28 is configured to, if the first accessory deviation metric is greater than a pre-determined accessory deviation threshold, generate a first accessory positioning guidance based at least in part on the determined first accessory deviation metric. In some examples, the first accessory positioning guidance includes guidance for positioning the patient relative to the accessory. In some examples, the accessory module 28 is configured to acquire a second accessory position and determine a second accessory deviation metric based at least in part on the second accessory position and the reference accessory position. For example, the accessory module 28 is configured to determine the second accessory deviation metric based at least in part on comparing (e.g., determining a difference between) the second accessory position and the reference accessory position. and determine whether the second accessory deviation metric is greater than the pre-determined accessory deviation threshold. In various examples, the first accessory position corresponds to a position of an accessory (e.g., a medical accessory, such as a coil) before adjustment (e.g., according to the accessory positioning guidance), whereas the second accessory position corresponds to a position of the accessory after adjustment.

Figure 2:
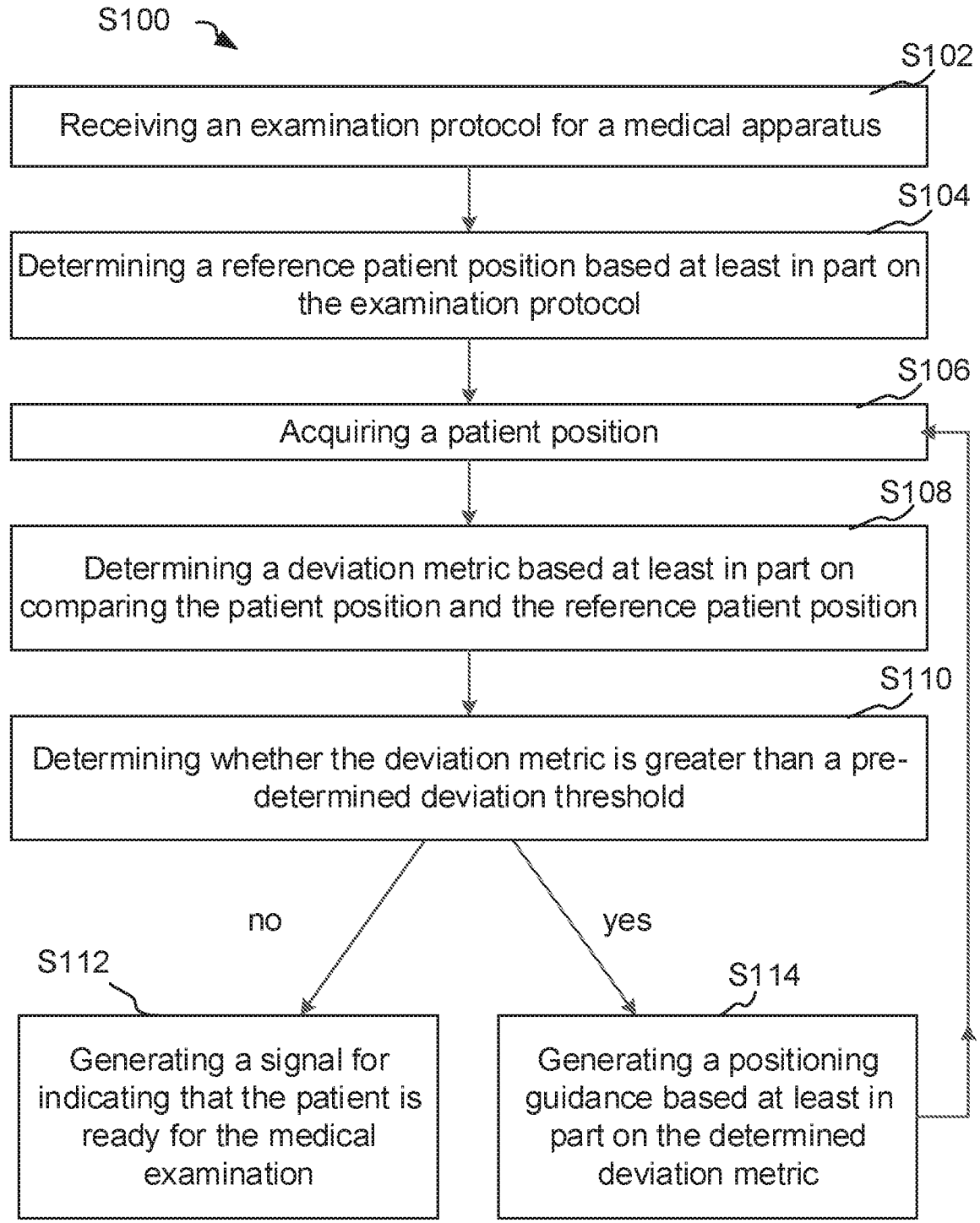
FIG. 2 is a simplified diagram showing a method for guiding a patient for a medical examination using a medical apparatus, according to some embodiments of the present invention.

FIG. 2 is a simplified diagram showing a method for guiding a patient for a medical examination using a medical apparatus, according to some embodiments of the present invention. This diagram is merely an example, which should not unduly limit the scope of the claims. One of ordinary skill in the art would recognize many variations, alternatives, and modifications. In some examples, the method S100 includes a process S102 of receiving an examination protocol for a medical apparatus, a process S104 of determining a reference position based at least in part on the examination protocol, a process S106 of acquiring a patient position, a process S108 of determining a deviation metric based at least in part on comparing the patient position and the reference position, a process S110 of determining whether the deviation metric is greater than a pre-determined deviation threshold, a process S112 of generating a signal for indicating the patient is ready for the medical examination if the deviation metric is not greater than the pre-determined deviation threshold, and/or a process S114 of generating a positioning guidance based at least in part on the determined deviation metric. In certain examples, one or more processes of the method S100 is repeated, such as after the patient and/or the medical apparatus is adjusted according to the positioning guidance. For example, the process S106, S108, and S110 are repeated after each patient adjustment. Although the above has been shown using a selected group of processes for the method, there can be many alternatives, modifications, and variations. For example, some of the processes may be expanded and/or combined. Other processes may be inserted to those noted above. Depending upon the embodiment, the sequence of processes may be interchanged with others replaced.

In some embodiments, the process S102 of receiving an examination protocol for a medical apparatus includes receiving an examination protocol selected by a user (e.g., a medical staff, a specialist, a physician), such as via a menu (e.g., a drop-down menu). In certain examples, the process S102 of receiving an examination protocol includes receiving the examination protocol selected from a plurality of pre-determined examination protocols. In various examples, the process S102 of receiving an examination protocol includes receiving the examination protocol generated by a trained protocol-generating model (e.g., a neural network). In some examples, the trained protocol-generating model is configured to generate the examination protocol based at least in part on patient information (e.g., medical condition, physical condition, and/or measurements), medical examination type, and/or target examination body part.

In some embodiments, the process S104 of determining a reference position based at least in part on the examination protocol includes determining the reference position based at least in part on one or more parameters corresponding to the examination protocol. In some examples, the process S104 of determining a reference position includes determining the reference position based at least in part on patient information (e.g., medical condition, physical condition, and/or measurements). In various examples, the process S104 of determining a reference position includes selecting the reference position from a plurality of pre-determined reference positions.

In some embodiments, the process S106 of acquiring a patient position includes acquiring a patient image and generating the patient position based at least in part on the patient image. In certain examples, acquiring the patient image includes acquiring the patient image using a sensor, such as a RGB sensor, a RGBD sensor, a laser sensor, a FIR sensor, a NIR sensor, and a lidar sensor. In various examples, generating the patient position based at least in part on the acquired patient image includes determining one or more internal landmarks associated with the acquired patient image. In some examples, the one or more internal landmarks includes one or more anatomical features. In certain examples, generating the patient position based at least in part on the acquired patient image includes determining one or more external landmarks associated with the acquired patient image. In some examples, the one or more external landmarks includes one or more non-anatomical objects.

In certain examples, generating the patient position based at least in part on the acquired patient image includes generating a patient representation. In certain examples, the first patient representation is two-dimensional or three-dimensional. In certain examples, the patient representation includes an image, a kinematic model, a skeleton model, a surface model, a mesh model, a point cloud, and/or a feature list including one or more features each having a corresponding coordinate. In various examples, the patient representation includes a parameterized human model. In some embodiments, the process S106 of acquiring a patient position is repeated after each time the patient position is adjusted (e.g., adjusted according to a patient positioning guidance).

In some embodiments, the process S108 of determining a deviation metric based at least in part on comparing the patient position and the reference position includes determining a reference vector based at least in part on the determined reference position, determining a patient vector based at least in part on the acquired patient position, determining a deviation vector based at least in part on the reference vector and the patient vector, and determining the deviation metric based at least in part on the deviation vector. In certain embodiments, determining the deviation metric includes receiving one or more anatomical features associated with the medical examination. In various examples, determining the deviation metric includes classifying the deviation vector as irrelevant if the deviation vector is determined based on an anatomical feature that is not included in the one or more anatomical features. In certain examples, determining the deviation metric includes classifying the deviation vector as relevant if the deviation vector is determined based on an anatomical feature that is included in the one or more anatomical features. In some embodiments, the process S108 of determining a deviation metric is repeated after each time the process S106 of acquiring a patient position is repeated, such as after each time the patient position is adjusted (e.g., adjusted according to a patient positioning guidance).

In some embodiments, the process S110 of determining whether the deviation metric is greater than a pre-determined deviation threshold includes selecting the pre-determined deviation threshold, such as via a menu. In other embodiments, the process S110 of determining whether the deviation metric is greater than a pre-determined deviation threshold includes determining whether the deviation metric is greater than or equal to the pre-determined deviation threshold. In some examples, the process S110 of determining whether the deviation metric is greater than a pre-determined deviation threshold includes comparing the deviation metric with one or more pre-determined deviation thresholds.

In some embodiments, the process S112 of generating a signal for indicating the patient is ready for the medical examination includes generating a signal for indicating that the patient is ready for the medical examination using an examination setting. In certain examples, the process S112 is performed if the deviation metric is not greater than the pre-determined deviation threshold.

In some embodiments, the process S114 of generating a positioning guidance based at least in part on the determined deviation metric includes generating a positioning guidance based at least in part on the determined deviation metric. In some examples, the positioning guidance includes guidance for positioning the patient relative to the medical apparatus. In some examples, generating the positioning guidance includes generating a visual guidance and/or an audio guidance. In certain examples, generating the visual guidance includes generating a visual representation on a display screen, a hologram in the three-dimensional space, a two-dimensional projection from a projector, an augmented reality representation in an augmented reality eyewear, a virtual reality representation in a virtual reality eyewear, and/or a lighting cue indicated by a light-emitting device. In various examples, generating the audio guidance includes generating an audio guidance having an audio volume corresponding to a magnitude of the deviation metric. In certain examples, generating the visual guidance includes generating an overlay highlighting the deviation metric associated with the acquired patient position (e.g., position before adjustment) and the reference position. For example, the overlay highlights showing differences between the acquired patient position and the reference position. In some examples, the method S100 further includes presenting the reference position for guiding the positioning of the patient. For example, the process S114 of generating a positioning guidance includes presenting the reference position. In certain examples, the process S114 is performed if the deviation metric is greater than or equal to the pre-determined deviation threshold.

In certain embodiments, the method S100 further includes detecting a foreign object based at least in part on an acquired patient image, generating a collision avoidance based at least in part on the foreign object. In certain examples, the generating the collision avoidance includes generating the collision avoidance based at least in part on the location and/or the dimensions of the foreign object. In certain examples, the collision avoidance includes a pause scan instruction, a stop scan instruction, an audio alert, a visual alert, and/or an overriding re-routing scan path (e.g., a path avoiding collision with the foreign object). In various examples, the detecting a foreign object is performed before and/or during the imaging (e.g., as part of the medical examination) of a patient, such as after a signal for indicating the patient is ready for the medical examination is generated.

In certain embodiments, the method S100 further includes determining the examination setting, the examination setting including a scanning path, a scanning angulation, a scanning parameter, a scanning speed, a scanning dose, and/or patient information. In certain examples, determining the examination setting includes determining the examination setting in real-time based at least in part on the reference position and/or the patient position. In various examples, determining the examination setting includes selecting the examination setting from a plurality of pre-determined examination settings.

In certain embodiments, the method S100 further includes presenting the positioning guidance continuously, such as presenting the positioning guidance live with real-time or near real-time update. In certain examples, the method S100 further includes presenting the positioning guidance statically, such as presenting the positioning guidance as fixed, such as until being updated with a new positioning guidance generated once the patient is adjusted and a new deviation metric is generated based on a newly acquired patient position.

In certain embodiments, the method S100 further includes determining a reference accessory position, acquiring an accessory position, determining an accessory deviation metric based at least in part on comparing the accessory position and the reference accessory position, and determining whether the accessory deviation metric is greater than a pre-determined accessory deviation threshold. In various examples, the method further includes generating a signal for indicating the accessory is in position for the medical examination if the deviation metric is not greater than the pre-determined deviation threshold and/or generating an accessory positioning guidance based at least in part on the determined accessory deviation metric if the first accessory deviation metric is greater than a pre-determined accessory deviation threshold. In various examples, the accessory positioning guidance includes guidance for positioning the patient relative to the accessory. In certain examples, determining a reference position, acquiring an accessory position, determining an accessory deviation metric, and/or determining whether the accessory deviation metric is greater than the pre-determined accessory deviation threshold is repeated, such as after the accessory and/or the medical apparatus is adjusted according to the accessory positioning guidance.

Figure 3:
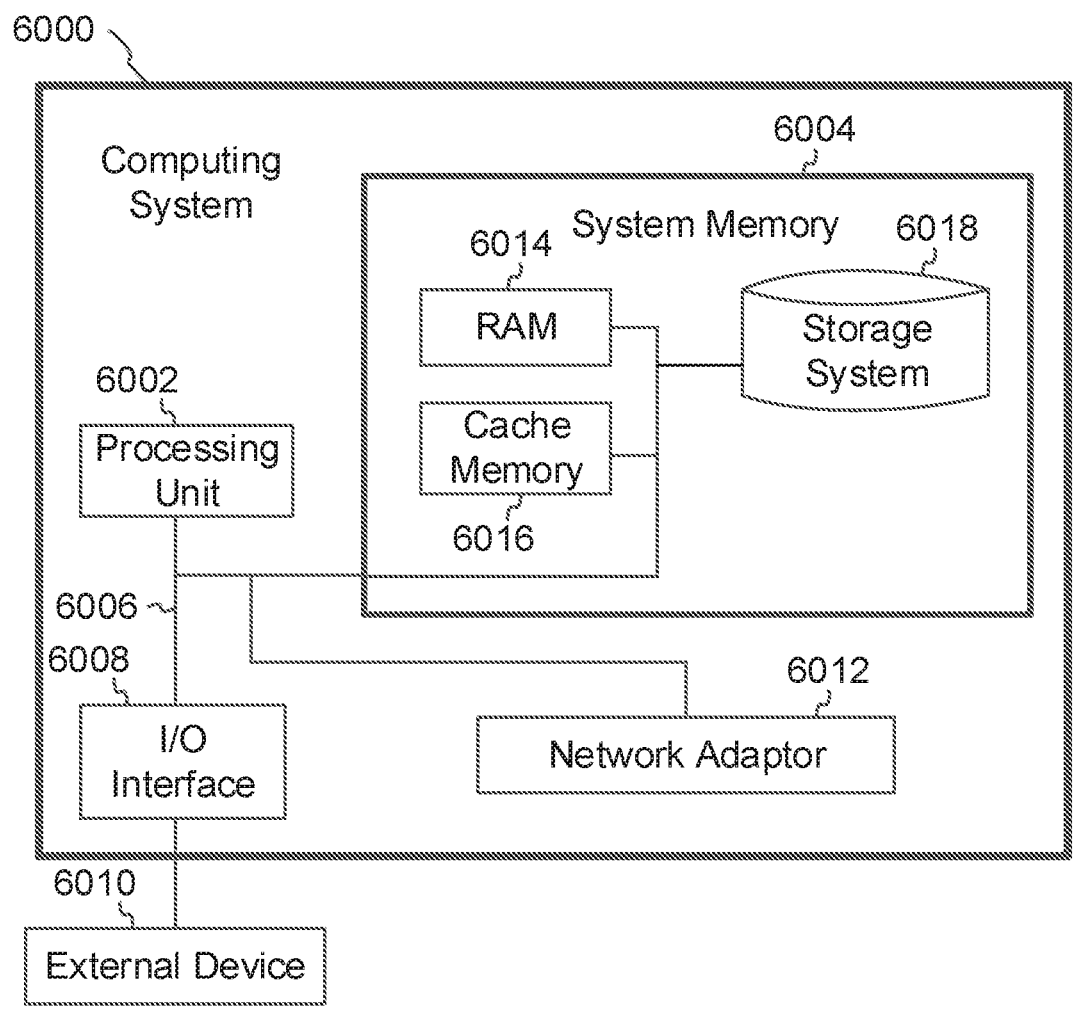
FIG. 3 is a simplified diagram showing a computing system, according to some embodiments of the present invention.

FIG. 3 is a simplified diagram showing a computing system, according to some embodiments. This diagram is merely an example, which should not unduly limit the scope of the claims. One of ordinary skill in the art would recognize many variations, alternatives, and modifications. In certain examples, the computing system 6000 is a general-purpose computing device. In some examples, the computing system 6000 includes one or more processing units 6002 (e.g., one or more processors), one or more system memories 6004, one or more buses 6006, one or more input/output (I/O) interfaces 6008, and/or one or more network adapters 6012. In certain examples, the one or more buses 6006 connect various system components including, for example, the one or more system memories 6004, the one or more processing units 6002, the one or more input/output (I/O) interfaces 6008, and/or the one or more network adapters 6012. Although the above has been shown using a selected group of components for the computing system, there can be many alternatives, modifications, and variations. For example, some of the components may be expanded and/or combined. Other components may be inserted to those noted above. Depending upon the embodiment, the arrangement of components may be interchanged with others replaced.

In certain examples, the computing system 6000 is a computer (e.g., a server computer, a client computer), a smartphone, a tablet, or a wearable device. In some examples, some or all processes (e.g., steps) of the method S100 are performed by the computing system 6000. In certain examples, some or all processes (e.g., steps) of the method S100 are performed by the one or more processing units 6002 directed by one or more codes. For example, the one or more codes are stored in the one or more system memories 6004 (e.g., one or more non-transitory computer-readable media), and are readable by the computing system 6000 (e.g., readable by the one or more processing units 6002). In various examples, the one or more system memories 6004 include one or more computer-readable media in the form of volatile memory, such as a random-access memory (RAM) 6014, a cache memory 6016, and/or a storage system 6018 (e.g., a floppy disk, a CD-ROM, and/or a DVD-ROM).

In some examples, the one or more input/output (I/O) interfaces 6008 of the computing system 6000 is configured to be in communication with one or more external devices 6010 (e.g., a keyboard, a pointing device, and/or a display). In certain examples, the one or more network adapters 6012 of the computing system 6000 is configured to communicate with one or more networks (e.g., a local area network (LAN), a wide area network (WAN), and/or a public network (e.g., the Internet)). In various examples, additional hardware and/or software modules are utilized in connection with the computing system 6000, such as one or more micro-codes and/or one or more device drivers.

Figure 4:
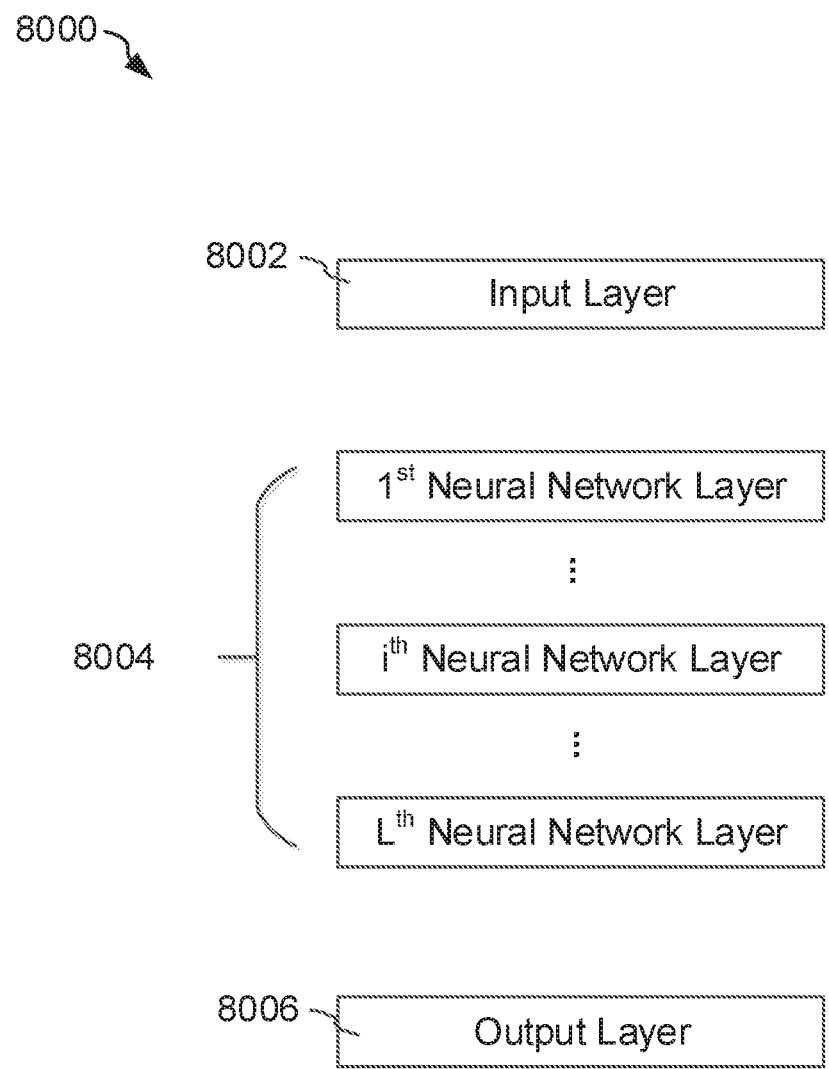
FIG. 4 is a simplified diagram showing a neural network, according to some embodiments of the present invention.

FIG. 4 is a simplified diagram showing a neural network, according to certain embodiments. This diagram is merely an example, which should not unduly limit the scope of the claims. One of ordinary skill in the art would recognize many variations, alternatives, and modifications. In some examples, the neural network 8000 includes an input layer 8002, one or more hidden layers 8004, and an output layer 8006. For example, the one or more hidden layers 8004 includes L number of neural network layers, which include a $1^{st}$ neural network layer, . . . , an $i^{th}$ neural network layer, . . . and an $L^{th}$ neural network layer, where L is a positive integer and i is an integer that is larger than or equal to 1 and smaller than or equal to L. Although the above has been shown using a selected group of components for the neural network, there can be many alternatives, modifications, and variations. For example, some of the components may be expanded and/or combined. Other components may be inserted to those noted above. Depending upon the embodiment, the arrangement of components may be interchanged with others replaced.

In some examples, some or all processes (e.g., steps) of the method S100 are performed by the neural network 8000 (e.g., using the computing system 6000). In certain examples, some or all processes (e.g., steps) of the method S100 are performed by the one or more processing units 6002 directed by one or more codes that implement the neural network 8000. For example, the one or more codes for the neural network 8000 are stored in the one or more system memories 6004 (e.g., one or more non-transitory computer-readable media), and are readable by the computing system 6000 such as by the one or more processing units 6002.

In certain examples, the neural network 8000 is a deep neural network (e.g., a convolutional neural network). In some examples, each neural network layer of the one or more hidden layers 8004 includes multiple sublayers. As an example, the $i^{th}$ neural network layer includes a convolutional layer, an activation layer, and a pooling layer. For example, the convolutional layer is configured to perform feature extraction on an input (e.g., received by the input layer or from a previous neural network layer), the activation layer is configured to apply a nonlinear activation function (e.g., a ReLU function) to the output of the convolutional layer, and the pooling layer is configured to compress (e.g., to down-sample, such as by performing max pooling or average pooling) the output of the activation layer. As an example, the output layer 8006 includes one or more fully connected layers.

In various embodiments, a computer-implemented method for guiding a patient for a medical examination using a medical apparatus includes: receiving an examination protocol for the medical apparatus; determining a reference position based at least in part on the examination protocol; acquiring a first patient position; determining a first deviation metric based at least in part on comparing the first patient position and the reference position; determining whether the first deviation metric is greater than a pre-determined deviation threshold; and if the first deviation metric is greater than a pre-determined deviation threshold: generating a first positioning guidance based at least in part on the determined first deviation metric, the first positioning guidance including guidance for positioning the patient relative to the medical apparatus. In certain examples, if the first deviation metric is greater than a pre-determined deviation threshold, the computer-implemented method further includes: acquiring a second patient position; determining a second deviation metric based at least in part on comparing the second patient position and the reference position; and determining whether the second deviation metric is greater than the pre-determined deviation threshold. In some examples, the computer-implemented method is implemented according to at least the method S100 of FIG. 2. In certain examples, the method is implemented by at least the system 10 of FIG. 1.

In some embodiments, determining a first deviation metric based at least in part on comparing the first patient position and the reference position includes: determining a reference vector based at least in part on the determined reference position; determining a first patient vector based at least in part on the acquired first patient position; determining a first deviation vector based at least in part on the reference vector and the first patient vector; and determining the first deviation metric based at least in part on the first deviation vector.

In some embodiments, determining a first deviation metric based at least in part on comparing the captured first patient position and the reference position further includes: receiving one or more anatomical features associated with the medical examination; classifying the first deviation vector as irrelevant if the first deviation vector is determined based on an anatomical feature that is not included in the one or more anatomical features; and classifying the first deviation vector as relevant if the first deviation vector is determined based on an anatomical feature that is included in the one or more anatomical features.

In some embodiments, acquiring a first patient position includes acquiring a first patient image and generating the first patient position based at least in part on the first patient image.

In some embodiments, the computer-implemented method further includes: detecting a foreign object based at least in part on the acquired first patient image; and generating a collision avoidance based at least in part on the foreign object. In certain examples, the collision avoidance includes at least one selected from a pause scan instruction, a stop scan instruction, an audio alert, a visual alert, and an overriding re-routing scan path.

In some embodiments, acquiring a first patient image includes acquiring the first patient image using at least one selected from a RGB sensor, a RGBD sensor, a laser sensor, a FIR sensor, a NIR sensor, and a lidar sensor.

In some embodiments, generating the first patient position based at least in part on the acquired first patient image includes determining one or more internal landmarks associated with the acquired first patient image, the one or more internal landmarks includes an anatomical feature.

In some embodiments, generating the first patient position based at least in part on the acquired first patient image includes determining one or more external landmarks associated with the acquired first patient image, the one or more external landmarks includes a non-anatomical object.

In some embodiments, generating the first patient position based at least in part on the acquired first patient image includes generating a first patient representation. In certain examples, the first patient representation is two-dimensional or three-dimensional. In certain examples, the patient representation includes at least one selected from an image, a kinematic model, a skeleton model, a surface model, a mesh model, a point cloud, and a feature list including one or more features each having a corresponding coordinate.

In some embodiments, the computer-implemented method further includes generating a signal for indicating that the patient is ready for the medical examination using an examination setting if the first deviation metric is smaller than or equal to the pre-determined deviation threshold.

In some embodiments, the computer-implemented method further includes determining the examination setting, the examination setting including at least one selected from a scanning path, a scanning angulation, a scanning parameter, a scanning speed, a scanning dose, and patient information. In certain examples, determining the examination setting includes one selected from: determining the examination setting in real-time based at least in part on one of the reference position and the first patient position; and selecting the examination setting from a plurality of pre-determined examination settings.

In some embodiments, the computer-implemented method further includes presenting the first positioning guidance continuously or statically.

In some embodiments, generating a first positioning guidance based at least in part on the determined first deviation metric includes generating at least one selected from a visual guidance and an audio guidance.

In some embodiments, generating a visual guidance includes: generating at least one selected from a visual representation on a display screen, a hologram in the three-dimensional space, a two-dimensional projection from a projector, an augmented reality representation in an augmented reality eyewear, a virtual reality representation in a virtual reality eyewear, and a lighting cue indicated by a light-emitting device.

In some embodiments, generating an audio guidance includes generating an audio guidance having an audio volume corresponding to a magnitude of the deviation metric.

In some embodiments, generating a visual guidance includes generating an overlay highlighting the first deviation metric associated with the first patient position and the reference position.

In some embodiments, the computer-implemented method further includes: determining a reference accessory position; acquiring a first accessory position; determining a first accessory deviation metric based at least in part on comparing the first accessory position and the reference accessory position; determining whether the first accessory deviation metric is greater than a pre-determined accessory deviation threshold; and if the first accessory deviation metric is greater than a pre-determined accessory deviation threshold: generating a first accessory positioning guidance based at least in part on the determined first accessory deviation metric, the first accessory positioning guidance including guidance for positioning the patient relative to the accessory; acquiring a second accessory position; determining a second accessory deviation metric based at least in part on comparing the second accessory position and the reference accessory position; and determining whether the second accessory deviation metric is greater than the pre-determined accessory deviation threshold.

In some embodiments, the computer-implemented method further includes presenting the reference position for guiding the positioning of the patient.

In various embodiments, a system for guiding a patient for a medical examination using a medical apparatus includes: a protocol receiving module configured to receive an examination protocol for the medical apparatus; a reference position determining module configured to determine a reference position based at least in part on the examination protocol; a patient position acquiring module configured to acquire a first patient position; a deviation metric determining module configured to determine a first deviation metric based at least in part on comparing the first patient position and the reference position; a positioning guidance module configured to: determine whether the first deviation metric is greater than a pre-determined deviation threshold; and if the first deviation metric is greater than a pre-determined deviation threshold: generate a first positioning guidance based at least in part on the determined first deviation metric. In certain examples, the first positioning guidance including guidance for positioning the patient relative to the medical apparatus. In certain examples, the patient position acquiring module is further configured to acquire a second patient position. In certain examples, the deviation metric determining module is further configured to determine a second deviation metric based at least in part on comparing the second patient position and the reference position. In certain examples, the positioning guidance module is further configured to determine whether the second deviation metric is greater than the pre-determined deviation threshold. In some examples, the system is implemented according to at least the system 10 of FIG. 1 and/or configured to perform at least the method S100 of FIG. 2.

In some embodiments, the deviation metric determining module is further configured to determine a reference vector based at least in part on the determined reference position; determine a first patient vector based at least in part on the acquired first patient position; determine a first deviation vector based at least in part on the reference vector and the first patient vector; and determine the first deviation metric based at least in part on the first deviation vector.

In some embodiments, the deviation metric determining module is further configured to determine one or more anatomical features associated with the medical examination; classify the first deviation vector as irrelevant if the first deviation vector is determined based on an anatomical feature that is not included in the one or more anatomical features; and classify the first deviation vector as relevant if the first deviation vector is determined based on an anatomical feature that is included in the one or more anatomical features.

In some embodiments, the patient position acquiring module is further configured to acquire a first patient image and generate the first patient position based at least in part on the first patient image.

In some embodiments, the system further includes a foreign object module configured to detect a foreign object based at least in part on the acquired first patient image; and generate a collision avoidance based at least in part on the foreign object. In certain examples, the collision avoidance includes at least one selected from a pause scan instruction, a stop scan instruction, an audio alert, a visual alert, and an overriding re-routing scan path.

In some embodiments, the patient position acquiring module is further configured to acquire the first patient image using at least one selected from a RGB sensor, a RGBD sensor, a laser sensor, a FIR sensor, a NIR sensor, and a lidar sensor.

In some embodiments, the patient position acquiring module is further configured to determine one or more internal landmarks associated with the acquired first patient image, the one or more internal landmarks includes an anatomical feature.

In some embodiments, the patient position acquiring module is further configured to determine one or more external landmarks associated with the acquired first patient image, the one or more external landmarks includes a non-anatomical object.

In some embodiments, the patient position acquiring module is further configured to generate a first patient representation. In certain examples, the first patient representation is two-dimensional or three-dimensional. In certain examples, the patient representation includes at least one selected from an image, a kinematic model, a skeleton model, a surface model, a mesh model, a point cloud, and a feature list including one or more features each having a corresponding coordinate.

In some embodiments, the system further includes a signaling module configured to generate a signal for indicating that the patient is ready for the medical examination using an examination setting if the first deviation metric is smaller than or equal to the pre-determined deviation threshold.

In some embodiments, the system further includes a settings module configured to determine the examination setting, the examination setting including at least one selected from a scanning path, a scanning angulation, a scanning parameter, a scanning speed, a scanning dose, and patient information. In certain examples, the settings module is further configured to determine the examination setting in real-time based at least in part on one of the reference position and the first patient position; and/or select the examination setting from a plurality of pre-determined examination settings.

In some embodiments, the positioning guidance module is further configured to present the first positioning guidance continuously or statically.

In some embodiments, the positioning guidance module is further configured to generate at least one selected from a visual guidance and an audio guidance.

In some embodiments, the positioning guidance module is further configured to generate at least one selected from a visual representation on a display screen, a hologram in the three-dimensional space, a two-dimensional projection from a projector, an augmented reality representation in an augmented reality eyewear, a virtual reality representation in a virtual reality eyewear, and a lighting cue indicated by a light-emitting device.

In some embodiments, the positioning guidance module is further configured to generate an audio guidance having an audio volume corresponding to a magnitude of the deviation metric.

In some embodiments, the positioning guidance module is further configured to generate an overlay highlighting the first deviation metric associated with the first patient position and the reference position.

In some embodiments, the system further includes an accessory module configured to: determine a reference accessory position; acquire a first accessory position; determine a first accessory deviation metric based at least in part on comparing the first accessory position and the reference accessory position; determine whether the first accessory deviation metric is greater than a pre-determined accessory deviation threshold; and if the first accessory deviation metric is greater than a pre-determined accessory deviation threshold: generate a first accessory positioning guidance based at least in part on the determined first accessory deviation metric, the first accessory positioning guidance including guidance for positioning the patient relative to the accessory; acquire a second accessory position; determine a second accessory deviation metric based at least in part on comparing the second accessory position and the reference accessory position; and determine whether the second accessory deviation metric is greater than the pre-determined accessory deviation threshold.

In some embodiments, the positioning guidance module is further configured to present the reference position for guiding the positioning of the patient.

In various embodiments, a non-transitory computer-readable medium with instructions stored thereon, that when executed by a processor, perform the processes including: receiving an examination protocol for the medical apparatus; determining a reference position based at least in part on the examination protocol; acquiring a first patient position; determining a first deviation metric based at least in part on comparing the first patient position and the reference position; determining whether the first deviation metric is greater than a pre-determined deviation threshold; and if the first deviation metric is greater than a pre-determined deviation threshold: generating a first positioning guidance based at least in part on the determined first deviation metric, the first positioning guidance including guidance for positioning the patient relative to the medical apparatus; acquiring a second patient position; determining a second deviation metric based at least in part on comparing the second patient position and the reference position; and determining whether the second deviation metric is greater than the pre-determined deviation threshold. In some examples, the non-transitory computer-readable medium with instructions stored thereon is implemented according to at least the method S100 of FIG. 2, and/or by the system 10 (e.g., a terminal) of FIG. 1.

In various embodiments, the non-transitory computer-readable medium with instructions stored thereon, that when executed by a processor, performing the process of determining a first deviation metric based at least in part on comparing the first patient position and the reference position includes: determining a reference vector based at least in part on the determined reference position; determining a first patient vector based at least in part on the acquired first patient position; determining a first deviation vector based at least in part on the reference vector and the first patient vector; and determining the first deviation metric based at least in part on the first deviation vector.

In some embodiments, the non-transitory computer-readable medium with instructions stored thereon, that when executed by a processor, perform the process of receiving one or more anatomical features associated with the medical examination; classifying the first deviation vector as irrelevant if the first deviation vector is determined based on an anatomical feature that is not included in the one or more anatomical features; and classifying the first deviation vector as relevant if the first deviation vector is determined based on an anatomical feature that is included in the one or more anatomical features.

In some embodiments, the non-transitory computer-readable medium with instructions stored thereon, that when executed by a processor, perform the process of acquiring a first patient image and generating the first patient position based at least in part on the first patient image.

In some embodiments, the non-transitory computer-readable medium with instructions stored thereon, that when executed by a processor, further perform the processes including detecting a foreign object based at least in part on the acquired first patient image; and generating a collision avoidance based at least in part on the foreign object. In certain examples, the collision avoidance includes at least one selected from a pause scan instruction, a stop scan instruction, an audio alert, a visual alert, and an overriding re-routing scan path.

In some embodiments, the non-transitory computer-readable medium with instructions stored thereon, that when executed by a processor, perform the process of acquiring the first patient image using at least one selected from a RGB sensor, a RGBD sensor, a laser sensor, a FIR sensor, a NIR sensor, and a lidar sensor.

In some embodiments, the non-transitory computer-readable medium with instructions stored thereon, that when executed by a processor, perform the process of determining one or more internal landmarks associated with the acquired first patient image, the one or more internal landmarks includes an anatomical feature.

In some embodiments, the non-transitory computer-readable medium with instructions stored thereon, that when executed by a processor, perform the process of determining one or more external landmarks associated with the acquired first patient image, the one or more external landmarks includes a non-anatomical object.

In some embodiments, the non-transitory computer-readable medium with instructions stored thereon, that when executed by a processor, perform the process of generating a first patient representation. In certain examples, the first patient representation is two-dimensional or three-dimensional. In certain examples, the patient representation includes at least one selected from an image, a kinematic model, a skeleton model, a surface model, a mesh model, a point cloud, and a feature list including one or more features each having a corresponding coordinate.

In some embodiments, the non-transitory computer-readable medium with instructions stored thereon, that when executed by a processor, further perform the processes including generating a signal for indicating that the patient is ready for the medical examination using an examination setting if the first deviation metric is smaller than or equal to the pre-determined deviation threshold.

In some embodiments, the non-transitory computer-readable medium with instructions stored thereon, that when executed by a processor, further perform the processes including determining the examination setting, the examination setting including at least one selected from a scanning path, a scanning angulation, a scanning parameter, a scanning speed, a scanning dose, and patient information. In certain examples, determining the examination setting includes one selected from: determining the examination setting in real-time based at least in part on one of the reference position and the first patient position; and selecting the examination setting from a plurality of pre-determined examination settings.

In some embodiments, the non-transitory computer-readable medium with instructions stored thereon, that when executed by a processor, further perform the processes including presenting the first positioning guidance continuously or statically.

In some embodiments, the non-transitory computer-readable medium with instructions stored thereon, that when executed by a processor, perform the process of generating at least one selected from a visual guidance and an audio guidance.

In some embodiments, the non-transitory computer-readable medium with instructions stored thereon, that when executed by a processor, perform the process of generating at least one selected from a visual representation on a display screen, a hologram in the three-dimensional space, a two-dimensional projection from a projector, an augmented reality representation in an augmented reality eyewear, a virtual reality representation in a virtual reality eyewear, and a lighting cue indicated by a light-emitting device.

In some embodiments, the non-transitory computer-readable medium with instructions stored thereon, that when executed by a processor, perform the process of generating an audio guidance includes generating an audio guidance having an audio volume corresponding to a magnitude of the deviation metric.

In some embodiments, the non-transitory computer-readable medium with instructions stored thereon, that when executed by a processor, perform the process of generating a visual guidance includes generating an overlay highlighting the first deviation metric associated with the first patient position and the reference position.

In some embodiments, the non-transitory computer-readable medium with instructions stored thereon, that when executed by a processor, further perform the processes including: determining a reference accessory position; acquiring a first accessory position; determining a first accessory deviation metric based at least in part on comparing the first accessory position and the reference accessory position; determining whether the first accessory deviation metric is greater than a pre-determined accessory deviation threshold; and if the first accessory deviation metric is greater than a pre-determined accessory deviation threshold: generating a first accessory positioning guidance based at least in part on the determined first accessory deviation metric, the first accessory positioning guidance including guidance for positioning the patient relative to the accessory; acquiring a second accessory position; determining a second accessory deviation metric based at least in part on comparing the second accessory position and the reference accessory position; and determining whether the second accessory deviation metric is greater than the pre-determined accessory deviation threshold.

In some embodiments, the non-transitory computer-readable medium with instructions stored thereon, that when executed by a processor, further perform the processes including presenting the reference position for guiding the positioning of the patient.

For example, some or all components of various embodiments of the present invention each are, individually and/or in combination with at least another component, implemented using one or more software components, one or more hardware components, and/or one or more combinations of software and hardware components. In another example, some or all components of various embodiments of the present invention each are, individually and/or in combination with at least another component, implemented in one or more circuits, such as one or more analog circuits and/or one or more digital circuits. In yet another example, while the embodiments described above refer to particular features, the scope of the present invention also includes embodiments having different combinations of features and embodiments that do not include all of the described features. In yet another example, various embodiments and/or examples of the present invention can be combined.

Additionally, the methods and systems described herein may be implemented on many different types of processing devices by program code including program instructions that are executable by the device processing subsystem. The software program instructions may include source code, object code, machine code, or any other stored data that is operable to cause a processing system to perform the methods and operations described herein. Other implementations may also be used, however, such as firmware or even appropriately designed hardware configured to perform the methods and systems described herein.

The systems' and methods' data (e.g., associations, mappings, data input, data output, intermediate data results, final data results, etc.) may be stored and implemented in one or more different types of computer-implemented data stores, such as different types of storage devices and programming constructs (e.g., RAM, ROM, EEPROM, Flash memory, flat files, databases, programming data structures, programming variables, IF-THEN (or similar type) statement constructs, application programming interface, etc.). It is noted that data structures describe formats for use in organizing and storing data in databases, programs, memory, or other computer-readable media for use by a computer program.

The systems and methods may be provided on many different types of computer-readable media including computer storage mechanisms (e.g., CD-ROM, diskette, RAM, flash memory, computer's hard drive, DVD, etc.) that contain instructions (e.g., software) for use in execution by a processor to perform the methods' operations and implement the systems described herein. The computer components, software modules, functions, data stores and data structures described herein may be connected directly or indirectly to each other in order to allow the flow of data needed for their operations. It is also noted that a module or processor includes a unit of code that performs a software operation and can be implemented for example as a subroutine unit of code, or as a software function unit of code, or as an object (as in an object-oriented paradigm), or as an applet, or in a computer script language, or as another type of computer code. The software components and/or functionality may be located on a single computer or distributed across multiple computers depending upon the situation at hand.

The computing system can include client devices and servers. A client device and server are generally remote from each other and typically interact through a communication network. The relationship of client device and server arises by virtue of computer programs running on the respective computers and having a client device-server relationship to each other.

This specification contains many specifics for particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations, one or more features from a combination can in some cases be removed from the combination, and a combination may, for example, be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Although specific embodiments of the present invention have been described, it will be understood by those of skill in the art that there are other embodiments that are equivalent to the described embodiments. Accordingly, it is to be understood that the invention is not to be limited by the specific illustrated embodiments.

What is claimed is:

1. A computer-implemented method for guiding a patient for a medical examination using a medical apparatus, the method comprising:

receiving an examination protocol for the medical apparatus;

determining, by one or more processors, a reference position based at least in part on the examination protocol;

acquiring a patient position;

determining, by the one or more processors, a deviation metric based at least in part on comparing the patient position and the reference position;

determining, by the one or more processors, whether the deviation metric is greater than a pre-determined deviation threshold; and if the deviation metric is greater than the pre-determined deviation threshold:

generating a positioning guidance based at least in part on the determined deviation metric, the positioning guidance including guidance for positioning the patient relative to the medical apparatus;

wherein the determining a deviation metric based at least in part on comparing the patient position and the reference position includes:
  determining a reference vector based at least in part on the determined reference position;
  determining a patient vector based at least in part on the acquired patient position;
  determining a deviation vector based at least in part on the reference vector and the patient vector; and
  determining the deviation metric based at least in part on the deviation vector.

2. The computer-implemented method of claim 1, wherein the determining a deviation metric based at least in part on comparing the captured patient position and the reference position further includes:
  receiving one or more anatomical features associated with the medical examination;
  classifying the deviation vector as irrelevant if the deviation vector is determined based on an anatomical feature that is not included in the one or more anatomical features; and
  classifying the deviation vector as relevant if the deviation vector is determined based on an anatomical feature that is included in the one or more anatomical features.

3. The computer-implemented method of claim 1, wherein the acquiring a patient position includes:
  acquiring a patient image; and
  generating the patient position based at least in part on the patient image.

4. The computer-implemented method of claim 3, further comprising:
  detecting a foreign object based at least in part on the acquired patient image; and
  generating a collision avoidance based at least in part on the foreign object;
  wherein the collision avoidance includes one selected from a pause scan instruction, a stop scan instruction, an audio alert, a visual alert, and an overriding re-routing scan path.

5. The computer-implemented method of claim 3, wherein the acquiring a patient image includes:
  acquiring the patient image using at least one selected from a RGB sensor, a RGBD sensor, a laser sensor, a far infrared ("FIR") sensor, a near infrared ("NIR") sensor, and a lidar sensor.

6. The computer-implemented method of claim 3, wherein the generating the patient position based at least in part on the acquired patient image includes:
  determining one or more internal landmarks associated with the acquired patient image, the one or more internal landmarks includes an anatomical feature.

7. The computer-implemented method of claim 3, wherein the generating the patient position based at least in part on the acquired patient image includes:
  determining one or more external landmarks associated with the acquired patient image, the one or more external landmarks includes a non-anatomical object.

8. The computer-implemented method of claim 3, wherein the generating the patient position based at least in part on the acquired patient image includes:
  generating a patient representation;
  wherein the patient representation is two-dimensional or three-dimensional;
  wherein the patient representation includes one selected from an image, a kinematic model, a skeleton model, a surface model, a mesh model, a point cloud, and a feature list including one or more features each having a corresponding coordinate.

9. The computer-implemented method of claim 1, further comprising:
  generating a signal for indicating that the patient is ready for the medical examination using an examination setting if the deviation metric is smaller than or equal to the pre-determined deviation threshold.

10. The computer-implemented method of claim 9, further comprising:
  determining the examination setting, the examination setting including one selected from a scanning path, a scanning angulation, a scanning parameter, a scanning speed, a scanning dose, and patient information;
  wherein determining the examination setting includes one selected from:
    determining the examination setting in real-time based at least in part on one of the reference position and the patient position; and
    selecting the examination setting from a plurality of pre-determined examination settings.

11. The computer-implemented method of claim 1, further comprising:
  presenting the positioning guidance continuously or statically.

12. The computer-implemented method of claim 11, wherein the generating a visual guidance includes:
  generating at least one selected from a visual representation on a display screen, a hologram in the three-dimensional space, a two-dimensional projection from a projector, an augmented reality representation in an augmented reality eyewear, a virtual reality representation in a virtual reality eyewear, and a lighting cue indicated by a light-emitting device.

13. The computer-implemented method of claim 11, wherein the generating an audio guidance includes:
  generating an audio guidance having an audio volume corresponding to a magnitude of the deviation metric.

14. The computer-implemented method of claim 11, wherein the generating a visual guidance includes:
  generating an overlay highlighting the deviation metric associated with the patient position and the reference position.

15. The computer-implemented method of claim 1, wherein the generating a positioning guidance based at least in part on the determined deviation metric includes:
  generating at least one selected from a visual guidance and an audio guidance.

16. The computer-implemented method of claim 1, further comprising:
  determining a reference accessory position;
  acquiring an accessory position;
  determining an accessory deviation metric based at least in part on comparing the accessory position and the reference accessory position;
  determining whether the accessory deviation metric is greater than a pre-determined accessory deviation threshold; and
  if the accessory deviation metric is greater than the pre-determined accessory deviation threshold:
    generating an accessory positioning guidance based at least in part on the determined accessory deviation metric, the accessory positioning guidance including guidance for positioning the patient relative to the accessory.

17. The computer-implemented method of claim 1, further comprising:
presenting the reference position for guiding the positioning of the patient.

18. A system for guiding a patient for a medical examination using a medical apparatus, the system comprising:
a protocol receiving module implemented on one or more processors and configured to receive an examination protocol for the medical apparatus;
a reference position determining module implemented on the one or more processors and configured to determine a reference position based at least in part on the examination protocol;
a patient position acquiring module implemented on the one or more processors and configured to acquire a patient position;
a deviation metric determining module implemented on the one or more processors and configured to determine a deviation metric based at least in part on comparing the patient position and the reference position;
a positioning guidance module implemented on the one or more processors and configured to:
determine whether the deviation metric is greater than a pre-determined deviation threshold; and
if the deviation metric is greater than a pre-determined deviation threshold:
generate a positioning guidance based at least in part on the determined deviation metric, the positioning guidance including guidance for positioning the patient relative to the medical apparatus;
wherein the deviation metric determining module is further configured to:
determine a reference vector based at least in part on the determined reference position;
determine a patient vector based at least in part on the acquired patient position;
determine a deviation vector based at least in part on the reference vector and the patient vector; and
determine the deviation metric based at least in part on the deviation vector.

19. A non-transitory computer-readable medium with instructions stored thereon, that when executed by a processor, perform the processes comprising:
receiving an examination protocol for the medical apparatus;
determining a reference position based at least in part on the examination protocol;
acquiring a patient position;
determining a deviation metric based at least in part on comparing the patient position and the reference position;
determining whether the deviation metric is greater than a pre-determined deviation threshold; and
if the deviation metric is greater than the pre-determined deviation threshold:
generating a positioning guidance based at least in part on the determined deviation metric, the positioning guidance including guidance for positioning the patient relative to the medical apparatus;
wherein the determining a deviation metric based at least in part on comparing the patient position and the reference position includes:
determining a reference vector based at least in part on the determined reference position;
determining a patient vector based at least in part on the acquired patient position;
determining a deviation vector based at least in part on the reference vector and the patient vector; and
determining the deviation metric based at least in part on the deviation vector.

* * * * *